United States Patent [19]

Von den Hoff

[11] 4,094,909

[45] June 13, 1978

[54] PROCESS FOR THE DECARBOXYLATION-OXIDATION OF BENZOIC ACID COMPOUNDS

[75] Inventor: Johan P. H. Von den Hoff, Geleen, Netherlands

[73] Assignee: Stamicarbon, B.V., Geleen, Netherlands

[21] Appl. No.: 773,127

[22] Filed: Feb. 28, 1977

[30] Foreign Application Priority Data

Feb. 28, 1976 Netherlands .......................... 7602078
Aug. 27, 1976 Netherlands .......................... 7609526

[51] Int. Cl.$^2$ .................... C07C 45/24; C07C 27/26; C07C 27/00; C07C 29/24
[52] U.S. Cl. ................ 206/586 P; 260/666 P; 260/674 H; 568/835; 568/799
[58] Field of Search ........... 260/586 P, 621 G, 631 H, 260/621 H, 666 P, 674 H, 622 R, 623 R, 620

[56] References Cited

U.S. PATENT DOCUMENTS

| | | | |
|---|---|---|---|
| 3,274,262 | 9/1966 | Albright et al. .................. | 260/621 G |
| 3,277,184 | 10/1966 | Ryland et al. .................... | 260/621 G |
| 3,288,865 | 11/1966 | Pontz ................................. | 260/621 G |
| 3,308,167 | 3/1967 | Costabello et al. ............. | 260/621 G |
| 3,349,134 | 10/1967 | Blom et al. ....................... | 260/621 G |
| 3,356,744 | 12/1967 | Woodward ....................... | 260/621 G |
| 3,365,503 | 1/1968 | Forni et al. ....................... | 260/621 G |
| 3,379,774 | 4/1968 | Forni et al. ....................... | 260/621 G |
| 3,639,452 | 2/1972 | Strojing et al. ................. | 260/621 G |
| 3,929,911 | 12/1975 | Van Dierendonck et al. ... | 260/621 G |

*Primary Examiner*—Norman Mogenstern
*Attorney, Agent, or Firm*—Cushman, Darby & Cushman

[57] ABSTRACT

A process for the decarboxylation-oxidation of a substituted or unsubstituted benzoic acid compound including heating the benzoic acid compound and forming a liquid phase, passing molecular oxygen in the presence of a copper catalyst through the hot liquid phase to form a substituted or unsubstituted phenol compound and a viscous tar-like product, and hydrogenating the viscous tar-like compound to form at least one low-boiling organic compound.

19 Claims, No Drawings

PROCESS FOR THE DECARBOXYLATION-OXIDATION OF BENZOIC ACID COMPOUNDS

BACKGROUND OF THE INVENTION

This application corresponds to Netherlands patent application Nos. 7602078, filed Feb. 28, 1976, and 7609526, filed Aug. 27, 1976, the disclosure of which is hereby incorporated by reference.

It is known that phenols can be prepared by treating a substituted or unsubstituted benzoic acid compound such as the acid or a salt, ester or anhydride thereof in the liquid phase and at an elevated temperature, with a molecular oxygen containing gas in the presence of a copper catalyst dissolved in the reaction mixture. The term "phenol" as used in this application includes both hydroxybenzene and ring substituted derivatives thereof. For example, the following phenol products can be prepared by this process from the indicated benzoic acid compound:

| Acid Starting Material | Phenol Product |
| --- | --- |
| Benzoic acid | Phenol |
| 2-Methylbenzoic acid | 3-Hydroxytoluene |
| 3-Methylbenzoic acid | 2- and 4-Hydroxytoluene |
| 4-Methylbenzoic acid | 3-Hydroxytoluene |
| 3-Nitrobenzoic acid | 4-Nitrophenol |
| 4-Nitrobenzoic acid | 3-Nitrophenol |
| 4-Chlorobenzoic acid | 3-Chlorophenol and Phenol |
| 4-Biphenylcarboxylic acid | 3-Hydroxybiphenyl |
| 2,4-Dimethylbenzoic acid | 2,5-Dimethylphenol |

See *Hydrocarbon Processing*, volume 43, pages 173 ff. (November 1965), which is hereby incorporated by reference. In this process of producing a phenol (as defined above), a tar-like product is also formed which until our invention has not been useful. Thus, until our invention it was customary to burn this tar-like product. In addition to being wasteful, this tar-like product often contained residues of the copper catalyst used. When the tar-like product was burned, the copper catalyst residues were sent into the atmosphere as copper oxides, etc., along with the combustion gases. Obviously, this is an environmental hazard, and costly equipment was necessary to remove the copper oxides from the combustion gases. Thus, in the practice of the prior art process not only was the tar-like product wasted, but copper catalyst itself was burned up, and costly equipment was required to remove the oxidized copper catalyst from the combustion gases.

SUMMARY OF THE INVENTION

Briefly, in accordance with the invention, a process for the decarboxylation-oxidation of substituted or unsubstituted benzoic acid compounds is disclosed. The benzoic acid compound in a liquid phase is heated and subjected to decarboxylation-oxidation by reaction with molecular oxygen in the presence of a copper catalyst. The decarboxylation-oxidation reaction produces a substituted or unsubstituted phenol compound and a viscous tar-like product. The tar-like product is subjected to hydrogenation to form at least one low-boiling organic compound.

Accordingly, it is an object of the present invention to provide a method of using the viscous tar-like product of the decarboxylation-oxidation of benzoic acid compounds.

Another object of the present invention is to recover any copper catalyst which may be contained in the viscous tar-like product of the decarboxylation-oxidation of benzoic acid compounds.

Yet, another object of the present invention is to form a maximum amount of a low-boiling organic compound such as cyclohexanol or cyclohexanone with the most efficient utilization of benzoic acid starting material and a minimum energy consumption in arranging the reaction conditions.

Other objects of the invention will be apparent from the detailed description of the invention and the claims which follow.

DETAILED DESCRIPTION OF THE INVENTION

In the process of the present invention, a substituted or unsubstituted benzoic acid compound is subjected to a decarboxylation-oxidation reaction with molecular oxygen in the presence of a copper catalyst to form a substituted or unsubstituted phenol compound, and a viscous tar-like product. The viscous tar-like product is hydrogenated to form at least one low-boiling organic compound. Substituted or unsubstituted benzoic acid compounds within the scope of the present invention include benzoic acid, benzoic acid salts such as alkali metal salts, benzoic acid esters such as $C_1$–$C_4$ alkyl or phenyl esters, and benzoic acid anhydrides. Any of these benzoic acid compounds may be substituted with any substituent, such as alkyl, halo, alkoxy, nitro, amino, or hydroxy. Typical benzoic acids are listed, for example, in R. Morrison and R. Boyd, *Organic Chemistry* Sec. 16.14 (Allyn and Bacon 1959). In the decarboxylation-oxidation reaction of a substituted or unsubstituted benzoic acid compound, the compound to be subject to decarboxylation-oxidation must be both heated and formed in a liquid phase. The decarboxylation-oxidation reaction is generally conducted at a temperature in the range of about 200° to about 300° C, and at a pressure of about 0.1 to about 10 atmospheres. The reaction pressure is preferably in the range of about 1 to about 3 atmospheres. The liquid phase containing the substituted or unsubstituted benzoic acid derivative may be formed either with or without a solvent. In the absence of a solvent, the substituted or unsubstituted benzoic acid compound is heated until it melts into a molten liquid phase. Alternatively, the substituted or unsubstituted benzoic acid compound may be dissolved in an inert solvent such as water or a liquid carboxylic acid.

The heated, liquid phase substituted or unsubstituted benzoic acid compound is reacted with a molecular oxygen-containing gas in the presence of a copper catalyst dissolved in the liquid phase containing the substituted or unsubstituted benzoic acid compound. The molecular oxygen containing gas may, for example, be air, pure oxygen, a mixture of air and oxygen or a mixture of air and nitrogen. Suitable copper catalysts for the decarboxylationoxidation reaction include copper (I) and copper (II) salts of carboxylic acids. Preferably, the copper catalyst is a copper (I) or copper (II) salt of the benzoic acid compound to be reacted. The preferred catalyst may be formed in the liquid phase reaction zone by introducing another copper compound, for instance, metallic copper or a copper salt such as copper (I) oxide, copper (II) oxide, or copper (II) salicylate into the liquid phase reaction zone. Metallic copper or the copper oxides or salicylate mentioned will react with the liquid phase benzoic acid compound in the reaction zone to form the preferred copper (I) or copper (II) salt of the benzoic acid compound to be subjected to decarboxylation-oxidation. The concentration of copper catalyst in the liquid phase reaction zone is generaly in the range of about 0.1 to about 5% by weight. In addition to the copper catalyst, a cocatalyst may also be present, for example, a soluble magnesium salt such as magnesium benzoate.

As illustrated above in the Background of the Invention, a decarboxylation-oxidation of a benzoic acid compound will form a phenol product which may be substituted or unsubstituted depending upon the benzoic acid starting material. It is to be noted that the substituent positions of the phenol product are not necessarily the same as the substituent positions of the benzoic acid starting material. The phenol product initially formed by the decarboxylation-oxidation reaction in the liquid phase reaction zone is generally a mixture of a phenol compound which may be substituted, as explained above, and a phenol benzoate. By passing steam through the liquid phase reaction zone, the phenol benzoate is hydrolyzed into phenol and benzoic acid (both of which may be substituted if the acid starting material was substituted), and the phenol compound can be separated and purified. By introducing steam into the liquid phase reaction zone at the same a gas-containing molecular oxygen is passed through the reaction zone to effect the decarboxylation-oxidation reaction, the phenol product can be separated in a single step rather than a two-step process.

The phenol product may be subjected to hydrogenation to form cyclohexanols and/or cyclohexanones depending upon the reaction conditions. The hydrogenation of phenols to form these products is described in British patent specification No. 890,095 which is hereby incorporated by reference. The cyclohexanols and cyclohexanones formed by the hydrogenation of the phenol product are easily separated, and are therefore of commercial importance.

In the decarboxylationoxidation of a benzoic acid compound, the ratio of phenol product to tar-like product produced will depend upon the reaction conditions as explained in *Hydrocarbon Processing* referenced above. In the past, the reaction conditions of the decarboxylation-oxidation reaction have been adjusted to produce the minimum possible amount of tar-like product, since the tar-like product was not considered to be useful. However, adjusting the reaction conditions of the decarboxylation-oxidation reaction to produce a minimum amount of the tar-like product is energy consuming. Thus, it is a particular advantage of the present invention that the energy consumed in the decarboxylation-oxidation reaction can be optimized in accordance with the particular benzoic acid compound used as a starting material since both the phenol product and the tar-like product are useful in the process of the present invention. The process of the present invention has particular utility in the preparation of cyclohexanone and/or cyclohexanol from benzoic acid. The production of a maximum amount of cyclohexanone and/or cyclohexanol from a minimum amount of benzoic acid with a minimum energy consumption is contemplated in the practice of the present invention. As those in the art are aware, cyclohexanol can be converted by dehydrogenation into cyclohexanone, which can be used as a starting material for the synthesis of caprolactam. The hydrogen gas set free in the dehydrogenation can well be used for the hydrogenation of the tar-like product.

Hydrogenating the viscous tar-like product formed in the decarboxylation-oxidation reaction converts the tar-like product into one or more low-boiling organic substances such as benzene, phenol, cyclohexane, cyclohexanol and cyclohexone. These low-boiling organic substances may be substituted in the ring. It is a particular advantage of the process of the present invention that the viscous tar-like product of the decarboxylation-oxidation of a benzoic acid compound which has heretofore not been considered useful can be converted into useful organic compounds, as described. The tar-like product of the decarboxylation-oxidation reaction may be subjected to hydrogenation with or without first removing unreacted benzoic acid starting material. It is, however, preferred to first remove any unreacted benzoic acid starting material which may be present in the tar-like product. Unreacted benzoic acid starting material may be removed from the tar-like product by distillation or by extraction with a suitable extractant. Examples of suitable extractants are water, alcohols such as methanol, ethanol or butanol, or aqueous alkaline liquors; aromatic hydrocarbons such as benzene, toluene, xylene or diphenyl; halogen-substituted hydrocarbons such as chlorobenzene or trichloroethylene, diphenyl ether; or mixtures thereof. The unreacted benzoic acid starting material extracted can be returned to the decarboxylation-oxidation reactor.

Preferably, the hydrogenation of the tar-like product of the decarboxylation-oxidation reaction is carried out in the presence of a solvent for the tar. Suitable solvents are, for example, methanol, cyclohexanol, phenol, diphenyl ether, 2-methoxyethanol ("Methylcellosolve"), cyclohexane, toluene, diphenyl, dimethylformamide, trichloroethylene and similar solvents. The hydrogenation of the tar-like product is preferably carried out with molecular hydrogen as the hydrogenation agent. The tar-like product is preferably in the liquid phase. Generally the liquid phase tar-like product is the continuous phase and the molecular hydrogen gas is the dispersed phase in the hydrogenation reaction. However, the hydrogenation reaction may also be carried out in a trickle phase reactor in which the tar-like product liquid phase is the dispersed phase and the molecular hydrogen gas phase is the continuous phase.

The hydrogenation of the tar-like product of the decarboxylation-oxidation reaction may be carried out either with or without a catalyst. If the hydrogenation reaction is conducted in the absence of a catalyst, the reaction temperature is generally between about 400° and about 1200° C. If a catalyst is used in the hydrogenation reaction, the reaction temperature is generally between about 30° and about 500° C. The reaction pressure is not critical and may for example be between about 1 and about 500 atmospheres, although a gas pressure of up to 1000 atmospheres is possible. It is generally preferred to use a reaction pressure in the range of about 5 to about 300 atmospheres. Catalysts used in the hydrogenation reaction are generally metals from the groups IB, VIB, VIIB and VIII or compounds thereof such as the metal oxides. The catalysts may be used either individually, or in mixtures. Examples of suitable metals include copper, chromium, molybdenum, cobalt, nickel, palladium, rhodium and platinum. Preferably, the catalyst used in the hydrogenation reaction is applied to a carrier. The usual carrier materials, such as silica or alumina may be used.

Hydrogenation catalysts which are particularly useful in the process of the present invention include catalysts which are suitable for hydro-treatment and hydro-cracking. Catalysts of this type are well-known to those skilled in the art, and are described in texts such as W. N. N. Knight et al., *Modern Petroleum Technology*, pages 309-322 (1973) and J. E. Germain, *Catalytic Conversion of Hydrocarbons* (Academic Press 1969), both of which are hereby incorporated by reference. If a hydro-treatment or a hydro-cracking type catalyst is used in the hydrogenation reaction, the reaction temperature is generally in the range of about 200° to about 500° C. It is particularly preferred that the catalyst be a nickel-cobalt-molybdenum catalyst on a carrier material. An especially preferred composition for a nickel-cobalt-molybdenum catalyst contains from about 10 to about 20% by weight of NiO, about 5 to about 10% by weight of CoO, and about 50 to about 90% by weight of $MoO_3$. These weight percentages are with reference to the mass of the catalyst itself, without considering the carrier material. The particularly preferred nickel-cobalt-molybdenum catalyst has been found to have an optimum reaction temperature for the hydrogenation reaction in the temperature range between about 350° and about 400° C. Within this reaction temperature range, the particularly preferred nickel-cobalt-molybdenum catalyst produces a high yield of phenol at a high conversion rate.

The products of the hydrogenation of the tar-like product in the absence of a hydrogenation catalyst are primarily phenol and aromatic or cycloaliphatic hydrocarbons. The same products are obtained if the hydrogenation reaction is conducted with a hydro-cracking catalyst. As explained above, the phenol can be converted into cyclohexanone or cyclohexanol by the process described in British Patent Specification No. 890,095, incorporated herewith by reference. Thus, in the process of the present invention, the tar-like product of the decarboxylation-oxidation reaction can be converted with a high selectivity into cyclohexanol and cyclohexanone.

The hydrogenation catalyst used in the process of the present invention preferably does not promote cracking or isomerization reactions. Catalysts of this type are described in the literature and are commercially available. For example, suitable catalysts are those described in the literature for use in the hydrogenation of phenol. Reference is made to the *Stanford Research Institute Reports*, vol. 7, pp. 257-274 (1965); vol. 7A, pp. 251-253 (1968); and vol. 7B, pp. 186-189 (1976), each of which is hereby incorporated by reference. When these catalysts are used, it is preferred to conduct the hydrogenation reaction at a temperature in the range of about 100° to about 200° C and at a pressure in the range of about 50 to about 200 atmospheres. Too high a reaction temperature will promote cracking and isomerization reactions, which will decrease the yield of cyclohexanol and/or cyclohexanone. Of the Group VIII metals which are suitable as catalysts in the hydrogenation reaction, cobalt, nickel, palladium, rhodium and platinum are especially suitable catalysts. Any of the catalysts mentioned may be used alone, or in mixtures of two or more. The catalyst used is preferably placed on a carrier material such as carbon, silica, alumina or titanium oxide. Especially preferred catalysts include Raney nickel, and palladium and/or platinum on an alumina carrier.

The hydrogenation catalyst used is preferably present in the hydrogenation reaction in an amount such that there are between about 0.01 and about 10 liters of tar material per liter of catalyst per hour.

With regard to the amount of molecular hydrogen used in the hydrogenation reaction, the minimum amount is, of course, the amount required for the desired conversion of the tar-like material into low-boiling organic compounds as described. It is preferred, however, to use an excess amount of molecular hydrogen to avoid fouling the catalyst material.

With the solvents for the tarry mass mentioned above also tar fractions can be separated from the tarry mass and a tar fraction so obtained be hydrogenated to cyclohexanone and/or cyclohexanol.

A great advantage of the process according to the invention is that, after the hydrogenation, the copper compounds present in the tar or tar fraction are left behind in the hydrogenation reactor as finely divided metal. The metal can be removed therefrom in a simple manner and, if so desired, can be returned to the oxidation reactor after separation.

Those skilled in the art will recognize that the benzoic acid compound which is the starting material in the process of the present invention may be formed by the oxidation of toluene or another alkyl benzene compound. These oxidation reactions will also produce a tarlike product which may be treated by the process of the present invention to yield low-boiling organic compounds, especially with the use of a hydro-treatment or hydro-cracking catalyst. It is preferred that the tar-like product resulting from the oxidation of toluene or other alkyl benzene compound be mixed with the tar-like product from the decarboxylationoxidation reaction of the benzoic acid compound prior to the hydrogenation treatment. The combined tar-like products may then be treated together.

The present invention will now be illustrated with the aid of a number of Examples. It is, of course, understood that the present invention is not limited to the illustrated Examples, but includes all aspects of the invention as described above, and set forth in the claims which follow. The percentages given in the Examples in each case are percentages by weight, with reference to the reaction product (after any water present is separated).

EXAMPLE I

Benzoic acid was oxidized and decarboxylated for a period of 1 to 2 hours by introduction of air and steam into molten benzoic acid at a temperature of 240° to 260° C and in the presence of copper (II) benzoate as catalyst, with the discharge of a phenolcontaining vapor. The liquid residue obtained was extracted with water until virtually all benzoic acid had been removed, the benzoic acid separated from the aqueous phase and returned to the decarboxylationoxidation reaction. A tar-like product (product E) was obtained.

The tar-like product (E) was subjected to fractional extraction with methanol and cyclohexane an a fraction having a molar weight of 400 to 500, which consisted of molecules with, on an average, five benzene nuclei per molecule, was isolated.

A solution of 25 g of this fraction in 112 g of cyclohexane was transferred to an autoclave and 10 g of Raney nickel was added. Hydrogen gas was introduced into the autoclave at a pressure of 130 atm. and the pressure was maintained at this value. The reaction temperature was 175° C. After 3 hours, the reaction was stopped and the autoclave opened. 15 grams of pure cyclohexanol was recovered by distillation. In addition, some cyclohexane was recovered as the only low molecular weight by-product. There was also some residue.

EXAMPLE II 40 parts by weight of the product (E) obtained in Example I and 60 parts by weight of diphenylether (DPO) were pumped over 200 ml of catalyst at a rate of 135 ml/hour. The reaction temperature was kept at 465° C, and the hydrogen pressure was 200 atmospheres. The catalyst used was a hydrogenating catalyst consisting of 2.8% of NiO, 15.5% of $MoO_3$ and 1.4% of CoO on an alumina carrier (% by weight referred to the total mass. This catalyst is commerically available under the name of 'Ketjen Fine 164' manufactured by AKCO Chemie B.V. Prior to use, the catalyst was reduced with hydrogen.

The conversion was complete. The product contained 46% of benzene, 6% of cyclohexane; 13% of toluene, and 35% of unidentified other volatile components.

EXAMPLE III

A product (E)/DPO mixture in 40/60 weight ratio was treated with $H_2$ at a pumping rate of 192 ml/hour and a temperature of 375° C. The catalyst and reaction conditions were the same as in Example II.

The product contained 6% benzene + cyclohexane, 13% phenol, 7% toluene and 61% DPO. The remainder was volatile alkanes, aromatices and alkyl aromatics.

EXAMPLE IV

Example III was repeated, however, with a pump rate of 144 ml/hour and a reactor temperature of 440° C.

The product contained 53% benzene + cyclohexane, 17% $C_6$-hydrocarbons (other than benzene or cyclohexane), 5% phenol, 1% toluene, 1.2% DPO and, for the remainder, compounds having at most two aromatic rings per molecule, but not identified in more detail.

EXAMPLE V

A product (E)/DPO mixture (40/60 weight ratio) was passed over a quartz bed (in the absence of a catalyst) at a bed temperature of 500° C, a pump rate of 192 ml/hour, and a hydrogen pressure of 200 atmospheres.

The product contained 3% benzene + cyclohexane, 8% phenol, 3% toluene, and 52% DPO, and 34% alkanes, alkyl aromatics and aromatics.

Thus, it is apparent that there has been provided, in accordance with the invention, a process for the decarboxylation-oxidation of a substituted or unsubstituted benzoic acid compound that fully satisfies the objects, aims, and advantages set forth above. While the invention has been described in conjunction with various specific embodiments thereof, it is evident that there are many alternatives, modifications and variations which will be apparent to those skilled in the art in light of the foregoing description. Accordingly, it is intended to embrace all such alternatives, modifications, and variations as fall within the spirit and broad scope of the following claims.

What is claimed is:

1. A process for the decarboxylation-oxidation of a substituted or unsubstituted benzoic acid compound, comprising:

heating said substituted or unsubstituted benzoic acid compound and forming a liquid phase, reacting said liquid phase substituted or unsubstituted benzoic acid compound with molecular oxygen in the presence of a copper catalyst thereby forming a substituted or unsubstituted phenol compound by decarboxylation-oxidation of said substituted or unsubstituted benzoic acid compound and also forming a viscous tar-like product, and hydrogenating said viscous tar-like product to form at least one low-boiling organic compound selected from the group consisting of substituted or unsubstituted benzene, phenol, cyclohexane, cyclohexanol and cyclohexanone.

2. The process of claim 1 wherein said substituted or unsubstituted benzoic acid compound is heated in the absence of a solvent to a temperature sufficient to form a molten liquid phase.

3. The process of claim 1 wherein said substituted or unsubstituted benzoic acid compound is dissolved in an inert solvent and heated to a temperature in the range of 200° to 300° C.

4. The process according to claim 1 wherein said copper catalyst is a copper (I) or a copper (II) salt of said substituted or unsubstituted benzoic acid compound.

5. The process according to claim 1 in which said molecular oxygen containing gas is air, pure oxygen, a mixture of air and oxygen, or a mixture of air and nitrogen.

6. The process according to claim 1 including separating said substituted or unsubstituted phenol compound from said viscous tar-like product, and dissolving said viscous tar-like product in a solvent prior to hydrogenating said viscous tar-like product.

7. The process according to claim 1 including hydrogenating said viscous tar-like product with molecular hydrogen in the absence of a catalyst at a temperature in the range between 400° and 1200° C.

8. The process of claim 1 including hydrogenating said viscous tar-like product with molecular hydrogen in the presence of a catalyst consisting of at least one metal or metal oxide selected from the group consisting of copper, chromium, molybdenum, cobalt, nickel, palladium, rhodium, platinum and oxides thereof at a temperature between 30° and 500° C.

9. The process according to claim 1 including hydrogenating said viscous tar-like product with molecular hydrogen in the presence of a hydro-cracking catalyst at a temperature in the range of 200° to 500° C.

10. The process according to claim 9 wherein said hydro-cracking catalyst is a Ni/Co/Mo catalyst.

11. The process of claim 1 including recovering any copper catalyst contained in said viscous tar-like product after hydrogenating said viscous tar-like product.

12. The process of claim 1 including hydrogenating said viscous tar-like product with molecular hydrogen in the presence of a catalyst containing one or more metals selected from the group consisting of cobalt, nickel, palladium, rhodium and platinum at a temperature between 30° and 500° C.

13. The process of claim 12 including hydrogenating said viscous tar-like product with molecular hydrogen in the presence of at least one catalyst selected from the group consisting of Raney nickel, palladium and platinum.

14. The process of claim 1 including removing unreacted substituted or unsubstituted benzoic acid compound from said substituted or unsubstituted phenol compound and said viscous tar-like product prior to hydrogenating said viscous tar-like product.

15. The process of claim 1 wherein said low-boiling organic compound formed by hydrogenating said viscous tar-like product is selected from the group consisting of phenol, cyclohexanol and cyclohexanone.

16. The process of claim 1 wherein said phenol compound formed by decarboxylation-oxidation of said benzoic acid compound is unsubstituted phenol, said low-boiling organic compound formed by hydrogenating said viscous tar-like product is selected from the group consisting of cyclohexanol and cyclohexanone.

17. The process of claim 8 including hydrogenating said viscous tar-like product with molecular hydrogen in the presence of a catalyst at a temperature in the range 30° to 350° C.

18. The process according to claim 8 including hydrogenating said viscous tar-like product with molecular hydrogen in the presence of a catalyst at a temperature in the range of 100° to 200° C.

19. The process according to claim 1 including hydrogenating said viscous tar-like product with molecular hydrogen in a trickle phase reactor.

* * * * *